US00PP24668P2

(12) United States Plant Patent
Liston

(10) Patent No.: US PP24,668 P2
(45) Date of Patent: Jul. 22, 2014

(54) ***IPOMOEA* PLANT NAMED 'GRAND MARBLE'**

(50) Latin Name: *Ipomoea batatas*
Varietal Denomination: Grand Marble

(75) Inventor: Larry Liston, Oklahoma City, OK (US)

(73) Assignee: Amerinova Properties LLC, Bonsall, CA (US)

( * ) Notice: Subject to any disclaimer, the term of this patent is extended or adjusted under 35 U.S.C. 154(b) by 147 days.

(21) Appl. No.: 13/507,514

(22) Filed: Jul. 5, 2012

(51) Int. Cl.
*A01H 5/00* (2006.01)

(52) U.S. Cl.
USPC ..... Plt./258

(58) Field of Classification Search
USPC ..... Plt./258
See application file for complete search history.

*Primary Examiner* — Kent L Bell
(74) *Attorney, Agent, or Firm* — C. A. Whealy

(57) ABSTRACT

A new and distinct cultivar of *Ipomoea* plant named 'Grand Marble', characterized by its initially upright then trailing plant habit; freely branching habit, dense and bushy growth habit; rapid growth rate; and dark purple and green bi-colored cordate-shaped leaves.

1 Drawing Sheet

Botanical designation: *Ipomoea batatas.*
Cultivar denomination: 'GRAND MARBLE'.

BACKGROUND OF THE INVENTION

The present invention relates to a new and distinct cultivar of *Ipomoea* plant, botanically known as *Ipomoea batatas*, commercially referred to as ornamental sweet potato and hereinafter referred to by the name 'Grand Marble'.

The new *Ipomoea* plant is a naturally-occurring branch mutation of *Ipomoea batatas* 'Blackie', not patented. The new *Ipomoea* plant was discovered and selected by the Inventor on a single plant within a population of plants of 'Blackie' in a controlled greenhouse environment in Oklahoma City, Okla. in 2008.

Asexual reproduction of the new *Ipomoea* plant by cuttings in a controlled greenhouse environment in Oklahoma City, Okla. since 2008 has shown that the unique features of this new *Ipomoea* plant are stable and reproduced true to type in successive generations.

SUMMARY OF THE INVENTION

Plants of the new *Ipomoea* have not been observed under all possible environmental conditions and cultural practices. The phenotype may vary somewhat with variations in environment such as temperature and light intensity without, however, any variance in genotype.

The following traits have been repeatedly observed and are determined to be the unique characteristics of 'Grand Marble'. These characteristics in combination distinguish 'Grand Marble' as a new and distinct *Ipomoea* plant:

1. Initially upright then trailing plant habit.
2. Freely branching habit, dense and bushy growth habit.
3. Rapid growth rate.
4. Dark purple and green bi-colored cordate-shaped leaves.

Plants of the new *Ipomoea* can be compared to plants of the parent, 'Blackie'. Plants of the new *Ipomoea* differ primarily from plants of 'Blackie' in leaf color as plants of 'Blackie' have solid dark purple-colored leaves.

Plants of the new *Ipomoea* can be compared to plants of the *Ipomoea batatas* 'Sweet Caroline Sweetheart Purple', not patented. In side-by-side comparisons conducted in Oklahoma City, Okla., plants of the new *Ipomoea* differed from plants of 'Sweet Caroline Sweetheart Purple' in the following characteristics:

1. Plants of the new *Ipomoea* were more trailing than plants of 'Sweet Caroline Sweetheart Purple'.
2. Plants of the new *Ipomoea* and 'Sweet Caroline Sweetheart Purple' differed in leaf color as plants of 'Sweet Caroline Sweetheart Purple' had solid purple-colored leaves.

Plants of the new *Ipomoea* can also be compared to plants of the *Ipomoea batatas* 'NCORNSP-011MONTC', disclosed in U.S. Plant Pat. No. 21,743. In side-by-side comparisons conducted in Oklahoma City, Okla., plants of the new *Ipomoea* differed from plants of 'NCORNSP-011MONTC' in the following characteristics:

1. Plants of the new *Ipomoea* had large cordate-shaped leaves whereas plants of 'NCORNSP-011MONTC' have palmate-shaped leaves with deep lobes.
2. Plants of the new *Ipomoea* and 'NCORNSP-011MONTC' differed in leaf color as plants of 'NCORNSP-011MONTC' had solid purple-colored leaves.

BRIEF DESCRIPTION OF THE PHOTOGRAPHS

The accompanying colored photographs illustrate the overall appearance of the new *Ipomoea* plant showing the colors as true as it is reasonably possible to obtain in colored reproductions of this type. Colors in the photographs may differ slightly from the color values cited in the detailed botanical description which accurately describe the colors of the new *Ipomoea* plant.

The photograph at the bottom of the sheet comprises a side perspective view of typical plants of 'Grand Marble' grown in a container.

The photograph at the top of the sheet comprises a close-up view of a typical plant of 'Grand Marble'.

DETAILED BOTANICAL DESCRIPTION

The aforementioned photographs and following observations, measurements and values describe plants grown in 12.7-cm containers during the winter in a polyethylene-covered greenhouse in Oklahoma City, Okla. under cultural practices which closely approximate commercial *Ipomoea* production. During the production of the plants, day temperatures ranged from 10° C. to 32° C. and night temperatures ranged from 4° C. to 24° C. Plants were three months old when the photographs and description were taken. In the detailed description, color references are made to The Royal Horticultural Society Colour Chart, 2007 Edition, except where general terms of ordinary dictionary significance are used.

Botanical classification: *Ipomoea batatas* 'Grand Marble'.

Parentage: Naturally-occurring branch mutation of *Ipomoea batatas* 'Blackie', not patented.

Propagation:

*Type*.—By cuttings.

*Time to initiate roots*.—About 10 to 14 days at temperatures of 21° C. to 29° C.

*Time to produce a rooted young plant*.—About three weeks at temperatures of 21° C. to 29° C.

*Root description*.—Medium in thickness, fibrous; white in color.

*Rooting habit*.—Freely branching; medium density.

*Tuber description*.—Tuber development has not been observed on plants of the new *Ipomoea*.

Plant description:

*Plant habit*.—Initially upright then trailing plant habit; freely branching habit, dense and bushy habit; pinching enhances lateral branch development; vigorous growth habit and rapid growth rate.

*Plant height*.—About 12 cm.

*Plant diameter*.—About 19 cm by 24 cm.

Lateral branch description:

*Quantity per plant*.—About three primary lateral branches develop per plant.

*Length*.—About 14.2 cm.

*Diameter*.—About 4 mm.

*Internode length*.—About 1.4 cm.

*Strength*.—Strong.

*Texture*.—Sparsely pubescent.

*Color*.—Close to N92A.

Foliage description:

*Arrangement*.—Alternate, simple.

*Length*.—About 8 cm.

*Width*.—About 6.2 cm.

*Shape*.—Cordate.

*Apex*.—Acuminate.

*Base*.—Cordate.

*Margin*.—Entire.

*Texture, upper surface*.—Sparsely pubescent.

*Texture, lower surface*.—Glabrous; prominent venation.

*Venation pattern*.—Pinnate; arcuate.

*Color*.—Developing leaves, upper surface: Close to 146A. Developing leaves, lower surface: Close to 148B. Fully expanded leaves, upper surface: Close to N186A to N186B with random sectors and flecks, close to 137A; venation, close to N92A. Fully expanded leaves, lower surface: Slightly more grey than N186C with random sectors and flecks, close to 138B; venation, close to N92A.

*Petiole*.—Length: About 6.5 cm. Diameter: About 2.5 mm. Texture, upper and lower surfaces: Smooth, glabrous. Color, upper surface: Close to N186C. Color, lower surface: Close to N186C with random flecks, close to 138B.

Flower description: Flower development has not been observed on plants of the new *Ipomoea*.

Temperature tolerance: Plants of the new *Ipomoea* have been observed to tolerate temperatures from about 5° C. to about 40° C.

Pathogen & pest resistance: Plants of the new *Ipomoea* have not been observed to be resistant to pests and pathogens common to *Ipomoea* plants.

It is claimed:

1. A new and distinct *Ipomoea* plant named 'Grand Marble' as illustrated and described.

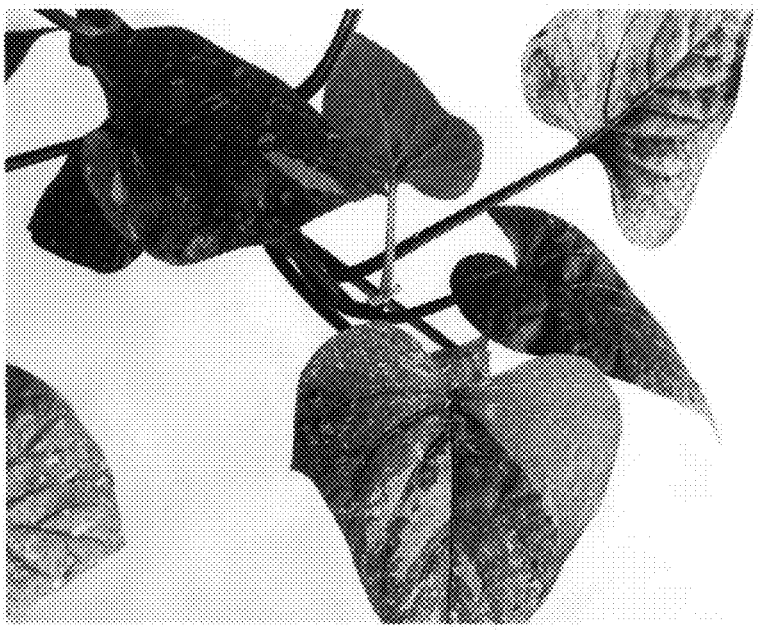
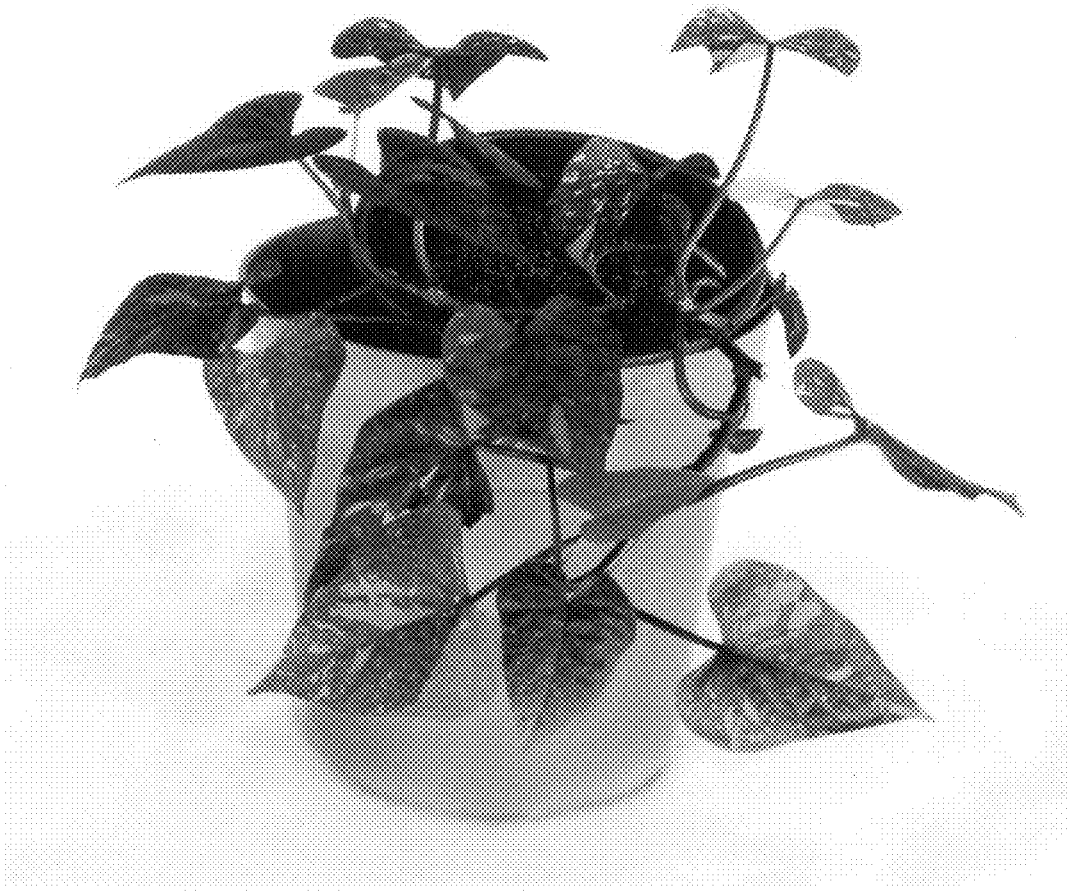

* * * * *